United States Patent [19]

Alaybayoglu et al.

[11] Patent Number: 4,823,244
[45] Date of Patent: Apr. 18, 1989

[54] LIGHT SOURCE ASSEMBLY

[75] Inventors: Erdem Alaybayoglu, Etobicoke; Ian D. Anderson, Fonthill; Robert J. Griffin, Richmond Hill, all of Canada

[73] Assignee: Niagara Medical Innovations Inc., Woodbridge, Canada

[21] Appl. No.: 150,336

[22] Filed: Jan. 29, 1988

[51] Int. Cl.$^4$ .............................................. F21L 11/00
[52] U.S. Cl. ..................................... 362/194; 362/32; 362/202; 362/253; 362/804; 128/6; 128/23
[58] Field of Search ................. 362/32, 194, 195, 202, 362/203, 208, 226, 253, 804; 128/6, 11, 13, 16, 18, 23

[56] References Cited

U.S. PATENT DOCUMENTS

| | | | |
|---|---|---|---|
| 3,582,638 | 6/1971 | Peters | 362/32 |
| 3,592,199 | 7/1971 | Ostensen | 362/32 X |
| 4,561,430 | 12/1985 | Walsh | 128/6 |
| 4,580,198 | 4/1986 | Zinnanti, Jr. | 362/804 X |

Primary Examiner—Stephen F. Husar

[57] ABSTRACT

A light source assembly comprises a lamp holder and a battery frame detachably attached thereto for mechanical and electrical connection.

20 Claims, 4 Drawing Sheets

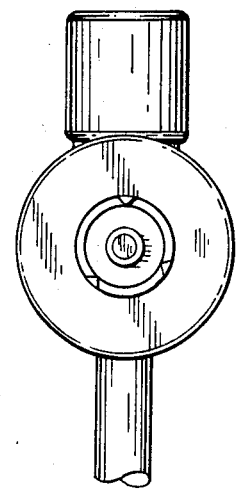
FIG. 3.
FIG. 3A.
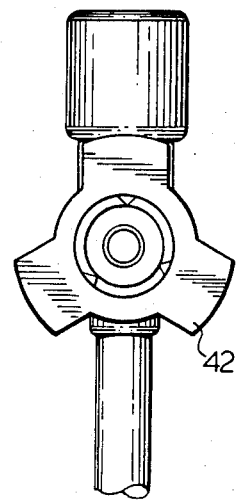

LIGHT SOURCE ASSEMBLY

This invention relates to a light source assembly for use with medical or industrial instruments. Emphasis herein will be given to the medical applications because such usage demonstrates adequately the character and nature of the invention which are also applicable to other fields, e.g. industrial boroscopy.

Medical instruments requiring a light source for surgery or exploratory work customarily employ glass fibres to conduct light from a bright source to the tip to illuminate the part of the body being inspected.

Such medical instruments include:
Audioscopes,
Nasopharynx, and Larynx Illuminators,
Laryngoscopes,
Anoscopes,
Telescopic, Non-telescopic Laparoscopes, (or Pelviscopes),
Proctoscopes,
Sigmoidoscopes,
Rectoscopes,
Illuminated Loupes,
Veterinary Diagnostic Instruments with light source,
Amnioscopes,
Cystoscopes,
Arthroscopes,
Emdoscopes, Present instruments are of the type shown in FIG. 1 where the instrument 10 although small enough to be handled by the surgeon must be connected to a relatively massive light source 12 by an optical fibre cable 14. The light source must contain a battery pack or mains connection. The instrument becomes difficult to use since its cable connection inhibits the manipulatory freedom of the surgeon. The cable length limits the doctor's operating locus relative to the light source or vice versa. The problems of sterilization are enormous.

Consideration by these applicants and possibly by others has been given to an instrument combined with a longitudinally arranged light source including a lamp and battery pack providing a hand held instrument resembling a "pen-light" flashlight in appearance. However, the power available from the aligned battery was not sufficient to provide the light intensity, candle power and colour temperature required to meet the surgeon's requirements. The requirement of sterility would have required special design to allow re-sterilization or the expense of providing an entirely disposable pack.

It is an object of this invention to provide a light source assembly comprising battery frame and lamp holder for assembly together, suitable to be detachably combined in an assembly with the instrument which has the fibre path to its tip. The assembly is light enough to be held in the hand and freely manipulable. The detachable assembly is designed to electrically and mechanically connect frame and holder. The arrangement allows the frame battery pack to be powerful enough to supply the illumination required. The two part assembly reduces the cost of sterilization since the lamp holder may be designed for re-use and sterilization whereas the batteries and frame may be designed to be disposable and hence to be provided in a sterile container, opened for use and discarded. The assembly of lamp holder and battery frame is designed for combination into a unit for use when hand-held by the surgeon.

It is a preferred object of the invention to provide a lamp holder and battery frame wherein the lamp holder is shaped to extend longitudinally and t define a longitudinally directed light path from a lamp mounted therein to an opening at one end and where the battery frame is detachably attachable thereto and laterally disposed therefrom to provide a light source assembly easily handled by the surgeon. The disposable battery frame may conveniently be designed to carry the necessary number of batteries to meet the illumination requirements and the lateral disposition provides a compact arrangement. It is a preferred aspect of the invention to design the components of the assembly so that the electrical connections between batteries and lamp also provide the detachable mechanical connections between the holder and frame.

In a preferred aspect of the invention, where the lamp holder has a thin longitudinally extending shape; the battery frame is designed to form a passage to receive the holder and for assembly by sliding longitudinally thereon. This can be achieved easily and conveniently in the operating room to attach and detach the disposable battery frame from the sterilizable light source holder. The arrangement lends itself to the simultaneous mechanical connection of the frame and holder and electrical connection of the battery and lamp. The arrangement of the frame in the form of a sleeve bout the holder, provides a compact and easily held assembly for manual retention and manipulation by the surgeon.

The preferred aspect of the invention as described in the preceding paragraph lends itself to further facilitation of assembly and disassembly since holder and frame may be designed so that the frame may be mechanically and electrically coupled to the holder in either orientation parallel to the longitudinal shape.

In drawings which illustrate a preferred embodiment of the invention:

FIG. 3 is an end view of the device as illustrated in FIG. 2, FIG. 3A is an end view of an alternate device within the scope of the invention.

Figure 1:
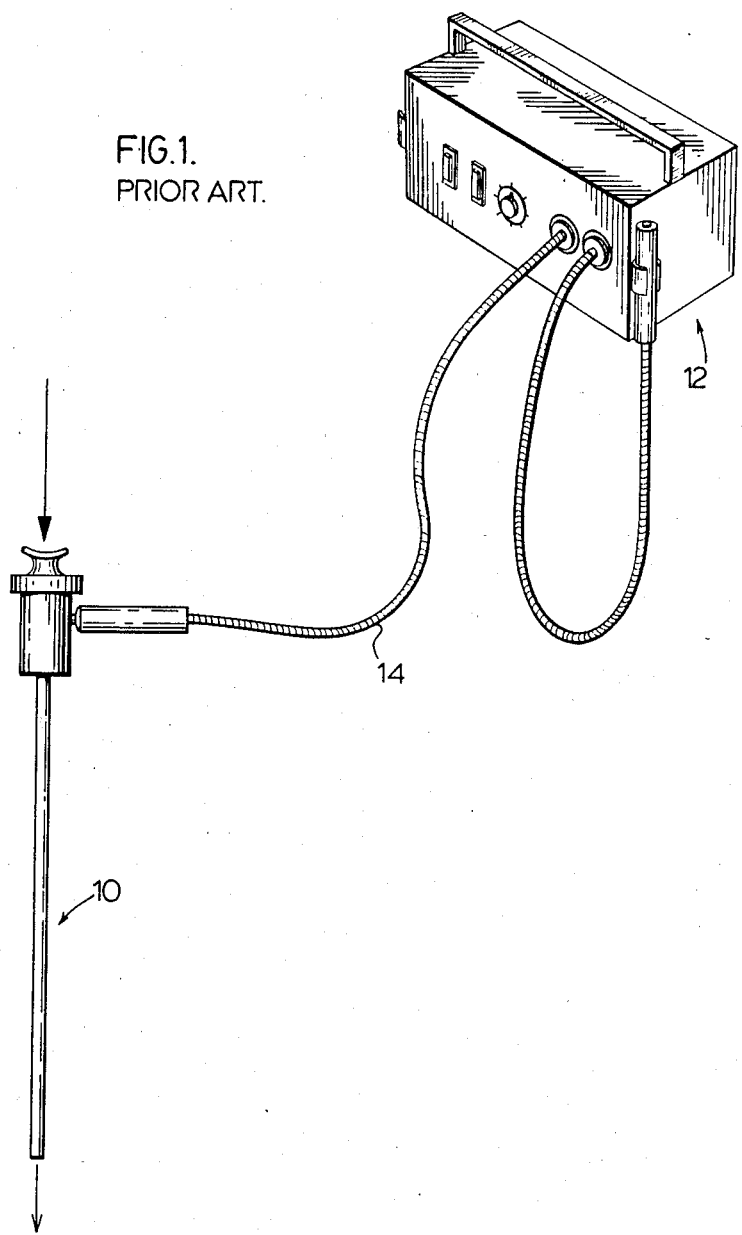
FIG. 1 shows the usual prior art arrangement.
Figure 2:
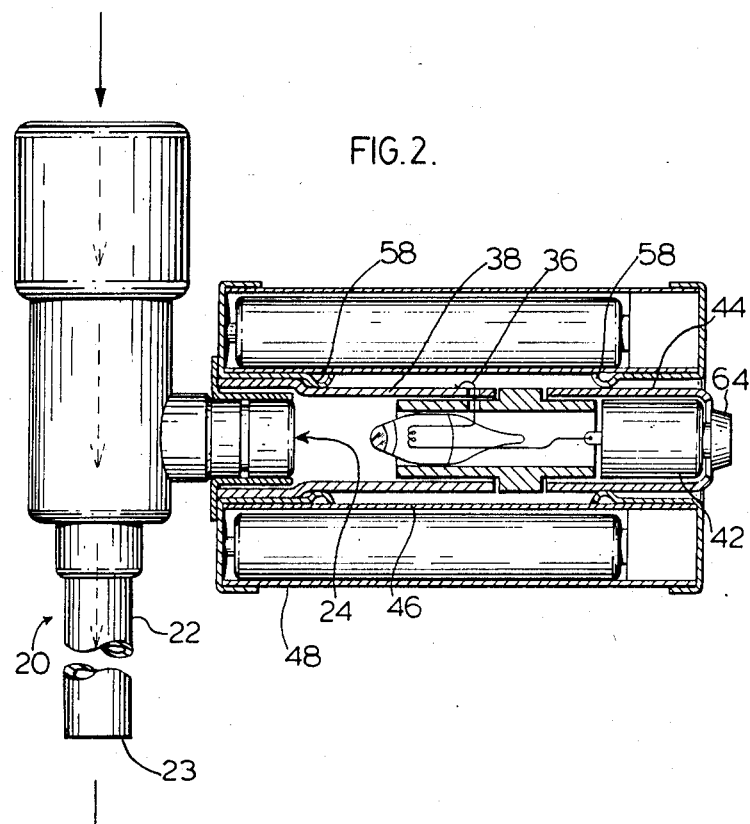
FIG. 2 is a vertical cross-section of the assembly combined with an observing instrument.

In the drawings 20 represents an endoscope as an example of the medical device with which the inventive device may be combined in a unit. As shown, the endoscope defines a vertical viewing path together through a tube 22, the tube 22 carries glass fibres surrounding the viewing path and carrying light to the instrument tip 23, that is from the tip remote to the tip adjacent end of the fibres. The tip remote end of the fibres are arranged at the lateral opening 24 of the instrument and form the light input end of the fibres.

The assembly will be formed to provide a convenient coupling to the light input end of the fibres and such coupling may be by any conventional means suitable to the instrument involved.

The light source assembly comprises a lamp holder 26 and a frame 28. The lamp holder preferably comprises a cylindrical tube 30 having a central raised ridge 32. A high intensity lamp 30 of suitable illumination quality is mounted in the tube to direct light to the forward end of the tube. The word 'forward' herein refers to direction in the assembly toward the endoscope and 'rearward' refer to the opposite direction. The lamp is preferably of the type where the forward end of the glass envelope of the bulb is formed into a focussing lens 34 to focus the light down the tube onto the tipremote end of the glass fibres. It is noted, with the type of lamps used, that the spacing between the lamp and the fibres (and adjacent portions of the instrument) must be sufficient that the heat from the lamp or instrument cannot melt, burn or damage the fibres or instrument. Electrically, one terminal of the lamp is led out through one aperture 36 in the tube wall forwardly of ridge 32 and into electrical contact with metal sleeve 38 to be described. The other terminal of the lamp is connected to one end of the potentiometer-switch arrangement 42 to be described and located rearwardly of the lamp 30 in the tube. The other end of the potentiometerswitch is electrically connected to the metal sleeve 44 extending about the tube rearward of the ridge 32. The forward and rearward sleeves are permanently attached to the exterior of the tube by any conventional means. The sleeves 38 and 44 form forward and rearward conducting areas for a series circuit including the lamp. The series circuit preferably includes an on-off switch as described. The sleeves and central ridge are designed so that the battery frame 28, to be described, may be shaped to slide longitudinally thereover from the rearward end of the holder.

Figure 5:
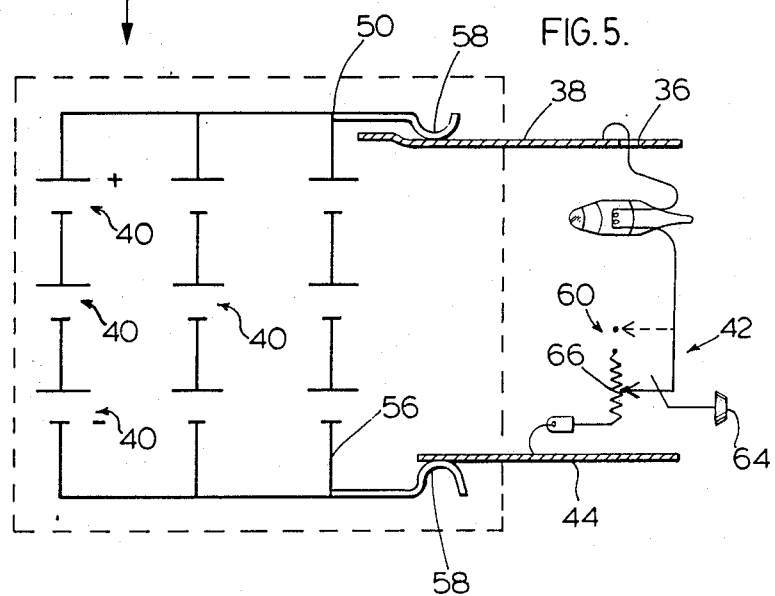
FIG. 5 shows a wiring design of the assembly.
Figure 6:
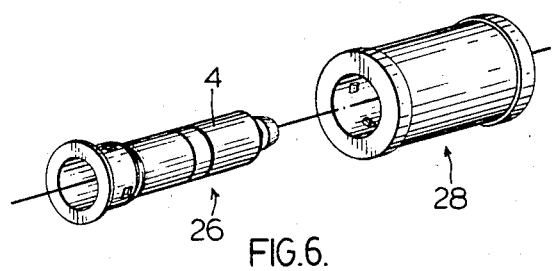
FIG. 6 shows lamp holder and battery frame ready for assembly.
Figure 4:
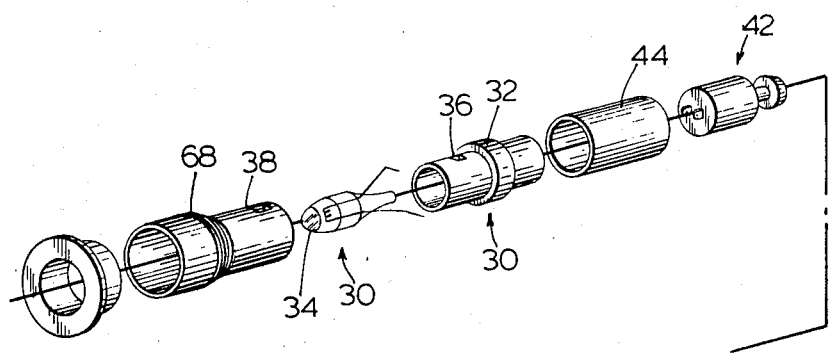
FIG. 4 shows an exploded view of the device of FIG. 2.
Figure 4:
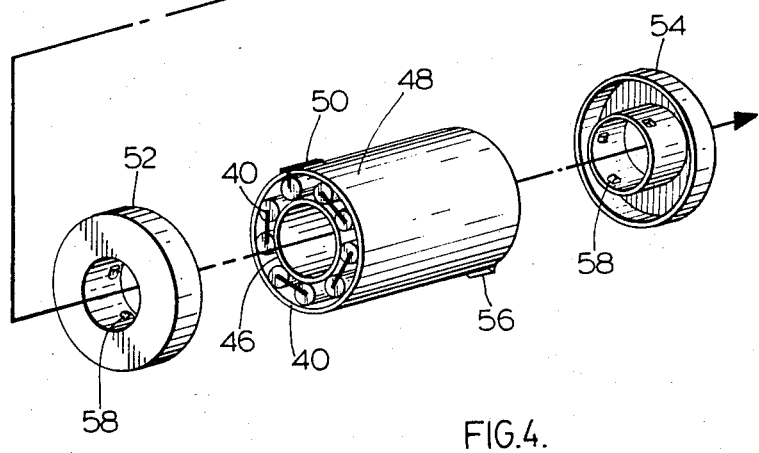

The frame 28 basically forms a sleeve or tube to be received onto the holder with batteries 40 laterally disposed from the holder. The sleeve will be shaped to compactly receive the required batteries for the power required. Here the batteries are arranged to form a cylinder. However, a splined arrangement may be provided as schematically shown in FIG. 3A with the batteries contained in the thick splines 42. In the preferred form shown in FIG. 3. 9×1.5 volt batteries 44 are arranged the periphery of the sleeve between inner and outer cylindrical covers 46 and 48. The batteries are arranged as shown in FIG. 3 and or 3A and connected in any desired manner to form the circuit disclosed in FIG. 5 with three sets of batteries in series circuits with the series circuits connected in parallel. The series-parallel circuit is provided with an output tab 50 brought outside the outer cover 48 at its forward end. Forward and rearward metal end caps 52 and 54 are provided to enclose the forward and rearward ends of the sleeve respectively to extend sufficiently far down the side of the cover 48 for electrical contact with the respective forward and rearward tabs 50 and 56. The caps may be retained in place by any desired means. The metal caps include inner walls designed to extend down the inner wall 46 of the frame and are provided with inwardly and directed slightly springy projections 58 to make electrical (and mechanical) contact with the forward and rearward sleeves 38 and 58 of the holder. Although, the batteries are connected in parallel to the extent described, the frame circuit, with the batteries considered collectively is a series circuit with the battery pack in series between end caps 52 and 54 and their projections 58.

The potentiometer 42 is preferably combined with on or off switch 60 shown schematically in the wiring diagram, (although these could also be provided separately). The design of the switch 60 will allow rotation of potentiometer knob 64 to switch the connection from OFF to ON and to vary series resistance 66 to allow control of lamp brightness by the surgeon.

The frame 28 is thus designed to be slid longitudinally onto the rearward end of the holder 20 and preferably in either longitudinal orientation of the frame. With the frame in place on the holder it will be seen that the respective projections 58 make contact with the forward and rearward sleeves 38 and 44 of the holder; and control the circuit subject to control by the ON-OFF potentiometer switch. In place on the holder, in assembly position, the frame and holder complete a series circuit including batteries and lamp and open or closed depending on the position of the ON-OFF switch. It will be noted that this circuit is independent of which end of the frame is on the forward end of the holder.

In the preferred embodiment the holder 20 and frame 28 are designed so that the frame, in each orientation is slid forwardly onto the holder to the assembly position.

A curved shoulder 68 on the forward sleeve of the holder supplies a forward stop to set the positioning of the frame on the holder. A ridge may also be provided on the rearward sleeve to be passed successively by the forward - located and rearward - located projections 58 of the frame and, when passed by the rearward projection, to form a positioner for the frame. However, in the preferred embodiment, the frame is retained on the holder, in assembly position, by friction. However, any detachable retaining means may be employed.

In operation (and assuming a surgical operating theatre), the sterile instrument and sterile holder are provided. A frame 28 is received in a sterile sealed package, opened and applied longitudinally to the holder 20 to provide the assembly. In place, the assembly is then coupled to the instrument 'light input' opening 24 by the designed conventional means. The surgeon may then turn the light ON at the potentiometer knob 64 and adjust the brightness from time to time as desired. The instrument is ready or use.

The batteries 40 will if desired to selected to provide longer illumination time than required. However, if they are exhausted in operation the frame 28 may quickly be discarded and a new frame 28 applied to the holder 20.

When the operation is completed the frames 28 are discarded and the holder 29 sterilized.

Preferred components and operating parameter arrangements are indicted below as exemplary only.

| 3.1 | Scope Lamp | | |
|---|---|---|---|
| 3.11 | Lamp | High Intensity light Corrected Spectrum Krypton gas filled enclosure Lens End. | 3.87* MSCP at spot 3300° K.** min. |
| | | C-6 Filament | Vibration and Shock Resistant. |
| | | End light output | 1120*** Footcandle |
| | | Spot Size | 0.160 Inch Nominal diameter measured in a transverse plane tangent to the lens. |
| 3.1.2 | Weight of Scope lamp Assy. | | <30 gm. |
| 3.1.3 | Washable and Sterilizable | | Not affected by normal hospital cleaning solutions, and autoclavable up to 300° F. |
| 3.1.4 | Adjustable Brightness | | 100%-60% |
| 3.1.5 | Attachable to all major endoscopes | | Wolf, Olympus, Stortz Heine, Winter & Ibe, Kli Acmi Pentax, etc. |
| 3.1.6 | Lamp life | | 25 Hrs. at 3.5 v. 70 Hrs. at 3.0 v. |
| 3.1.7 | Reliability | | No failure mode other than |

| | | |
|---|---|---|
| | | bulb. |
| 3.2 | Power Pak. (P/N 05-000617-01) | |
| 3.2.1 | Operating life | 35 min. at full brightness setting. voltage >2.9 at 10 min. voltage >2.5 at 30 min. |
| 3.2.2 | Pre-Sterilized | Ethylene oxide. Sterilized with double wrap protection. |
| 3.2.3 | Light Weight | <70 gm. |
| 3.2.4 | Shelf life | 6 months minimum. |
| 3.2.5 | Connection | by circular rings on pak centre hole. Pak mountable on lamp from either end. |

*MSCP (Mean Spherical Candle Power) in a 20 inch. Integrating Sphere.
**3300° K. at filament centre coils outer diameter, using a telescoping optical pyrometer.
***Through a 0.193 Inch aperture 0.050 Inch from the lamp lens surface and with the lamp 1.800 Inch ± 0.030 Inch from the detector surface. The light output is 1120 footcandles. This measurement shall be performed using an EG & G Model 550 Radiometer/Photometer system equipped with a 550-18 Cosine Photometric Probe.
Note: Average Procedure time is 10–15 minutes with usual maximum at 20 minutes.

Industrial applications include Borescopes of the types: micro borescopes, flexible borescopes, scan borescope, zoom borescopes, jet engine borescopes and internal diameter borescopes.

In the Industrial applications the sterile conditions will not usually be required.

We claim:

1. Light source assembly for instrument which instrument provides a glass fibre path to conduct light from a tip-remote to a tip-adjacent location, comprising:
   a holder for mounting a lamp defining a radiation path for said source,
   means for coupling said holder to said instrument designed to direct said radiation path onto the fibres at the tip remote location,
   a frame including at least one battery,
   said frame and holder being designed for sliding assembly and disassembly,
   means responsive to said assembly to connect said at least one battery to said light source.

2. Light source assembly as claimed in claim 1 wherein said holder and frame are designed so that when assembled said battery is disposed laterally from said holder relative to said light path.

3. Light source assembly as claimed in claim 1 wherein said holder is shaped to extend longitudinally generally parallel to said light path,
   said frame is designed to define a passage to receive said holder,
   and said frame and said holder are designed to be assembled by sliding said frame over the tip-remote end of said holder into assembled position.

4. Light source assembly as claimed in claim 3 wherein a pair of exterior surfaces on said holder for terminals form a lamp energization circuit, said frame is provided with a pair of surfaces facing said passage which form terminals for a circuit including said at least one battery, said holder and frame being designed to bring a different one of said holder surfaces into contact with each one said frame surfaces on assembly.

5. Light source assembly as claimed in claim 3 wherein a pair of exterior surfaces on said holder form terminals for a light energization circuit, said frame is provided with a pair of surfaces facing said passage which form terminals for a circuit for said at least one battery, said holder and frame being designed to bring each of the said holder surfaces into contact with a different one of said frame surfaces at assembly.

6. Light source assembly as claimed in claim 3 designed for operation when either end of said frame is slid over said holder.

7. Light source assembly as claimed in claim 4 designed for a product when either end of said frame is slid over said holder.

8. Light source assembly as claimed in claim 5 designed for a product when either end of said frame is slid over said holder.

9. Light source assembly for instrument which instrument provides a glass fibre path to conduct light from a tip-remote to a tip-adjacent location, and defining an illumination opening to said tip-remote location comprising:
   a holder having a thin longitudinally extending shape, containing a lamp,
   said holder defining a light path from said lamp, in said longitudinal direction, to an opening at one end of the said holder, whereby when said holder is applied to said instrument with said opening meeting said illumination opening said source will illuminate the tip-remote end of said fibres,
   said holder having conducting areas insulated from each other,
   each conducting area being electrically connected to a corresponding contact on said lamp,
   a frame defining a passage allowing it to be slid in the direction of the said path over the said holder, to an assembly position, and to be detachably retained in the said position,
   said frame carrying at least one battery,
   a pair of contacts facing said passage, each contact being electrically connected to one pole of said at least one battery,
   said holder contacts being arranged so that each makes electrical connection with one of said frame contacts in assembly position.

10. Light source assembly as claimed in claim 9 wherein said holder conducting areas are longitudinally spaced.

11. Light source assembly as claimed in claim 9 designed for a product when either end of said frame is slid over said holder.

12. Light source assembly as claimed in claim 10 designed for a product when either end of said frame is slid over said holder.

13. Light source assembly comprising:
   a holder for mounting a lamp defining a radiation path from said source,
   a frame including at least one battery,
   means for detachably assembling said frame to said holder,
   means responsive to said assembly to contact said at least one battery to said lamp to complete an illumination circuit for said lamp.

14. Light source assembly as claimed in claim 13 wherein said holder and frame are designed so that when assembled said battery is disposed laterally from said holder relative to said light path.

15. Light source assembly as claimed in claim 13 wherein said holder is shaped to extend longitudinally generally parallel to said light path,
   and said frame is designed to define a passage to receive said holder,
   and said frame and said holder are designed to be assembled by sliding said frame over one end of said holder into assembled position.

16. Light source assembly as claimed in claim 15 designed for a product when either end of said frame is slid over said holder.

17. Light source assembly comprising:

a holder, of thin longitudinally extending shape, containing a lamp, said holder defining a light path from said lamp, in said longitudinal direction to an opening at one end of said mount, said holder having external conducting areas insulated from each other, each conducting area forming two terminals of an electrical circuit including said light source, a frame designed to mount at least one battery, said frame defining a passage allowing it to be slid in the direction of said path over saidhholder to an assembly position, and to be detachably retained in said position, a pair of frame contacts facing said passage, each contact being electrically connected to one pole of said at least one battery, said holder areas being arranged so that each makes electrical connection with a different one of said frame contacts in assembled position.

18. Light source assembly as claimed in claim 17 wherein said holder conducting areas are longitudinally spaced.

19. Light source assembly as claimed in claim 17 designed for a product when either end of said frame is slid over said holder.

20. Light source assembly as claimed in claim 18 designed for a product when either end of said frame is slid over said holder.

* * * * *